United States Patent
Belk et al.

(10) Patent No.: US 8,064,996 B2
(45) Date of Patent: Nov. 22, 2011

(54) AUTOMATIC DETERMINATION OF T-SHOCK VULNERABLE WINDOW

(75) Inventors: Paul A. Belk, Maple Grove, MN (US); Jeffrey M. Gillberg, Coon Rapids, MN (US); Jian Cao, Shoreview, MN (US); Charles D. Swerdlow, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 1053 days.

(21) Appl. No.: 11/866,700

(22) Filed: Oct. 3, 2007

(65) Prior Publication Data

US 2009/0093860 A1    Apr. 9, 2009

(51) Int. Cl.
*A61N 1/39* (2006.01)
(52) U.S. Cl. .............................. 607/8; 607/9
(58) Field of Classification Search .......... 607/2, 4, 607/5, 9, 11, 26
See application file for complete search history.

(56) References Cited

U.S. PATENT DOCUMENTS

| | | | |
|---|---|---|---|
| 5,105,809 A | 4/1992 | Bach, Jr. et al. | |
| 5,346,506 A | 9/1994 | Mower et al. | |
| 5,564,422 A | 10/1996 | Chen et al. | |
| 5,954,753 A | 9/1999 | Alt et al. | |
| 6,477,422 B1 | 11/2002 | Splett | |
| 6,675,042 B2 | 1/2004 | Swerdlow et al. | |
| 6,834,204 B2 * | 12/2004 | Ostroff et al. | 607/2 |
| 7,181,275 B2 | 2/2007 | Havel | |
| 7,181,285 B2 | 2/2007 | Lindh et al. | |
| 7,257,441 B2 | 8/2007 | Swerdlow et al. | |
| 2003/0195569 A1 | 10/2003 | Swerdlow et al. | |
| 2004/0220631 A1 | 11/2004 | Burnes et al. | |
| 2005/0038478 A1 | 2/2005 | Klepfer et al. | |
| 2006/0235476 A1 | 10/2006 | Gunderson et al. | |
| 2009/0093860 A1 | 4/2009 | Belk et al. | |

FOREIGN PATENT DOCUMENTS

| | | |
|---|---|---|
| EP | 0597431 A2 | 5/1994 |
| WO | WO2006115940 A | 11/2006 |
| WO | 2009045610 A1 | 4/2009 |

OTHER PUBLICATIONS

Shehata et al. "Automatic Determination of Timing Intervals for upper limit of vulnerability using ICD Electrograms", PACE, vol. 31, Jun. 2008, pp. 691-700, XP002500636.
International Search Report, PCT/US2008/071144, Nov. 26, 2008, 9 Pages.

* cited by examiner

*Primary Examiner* — Carl H Layno
*Assistant Examiner* — Allen Porter, Jr.
(74) *Attorney, Agent, or Firm* — Michael C. Soldner (57) ABSTRACT

A method and apparatus for determining a T-wave shock interval sense a cardiac electrogram (EGM) signal comprising a T-wave signal. A T-wave center is determined from the EGM signal, and a T-wave shock interval is determined in response to determining the T-wave center. A T-wave shock is delivered at the T-wave shock interval computed based on the T-wave center.

17 Claims, 6 Drawing Sheets

AUTOMATIC DETERMINATION OF T-SHOCK VULNERABLE WINDOW

TECHNICAL FIELD

The invention relates generally to implantable medical devices and, in particular, to an automated method and apparatus for determining a time interval for delivering T-wave shocks to a patient's heart.

BACKGROUND

Delivery of a shock pulse during the vulnerable period of the cardiac cycle can induce fibrillation, providing the shock energy is greater than a patient-specific minimum value and less than a patient-specific maximum value. Such a shock pulse is generally referred to as a "T-shock" or "T-wave shock" because the time of the vulnerable period during the cardiac cycle generally corresponds to the T-wave of the ECG signal. The upper limit of vulnerability (ULV) is the shock strength at or above which fibrillation is not induced when a shock is delivered during the vulnerable period of a normal cardiac cycle. The minimum shock strength required to defibrillate the human heart, often referred to as the defibrillation threshold (DFT), corresponds quantitatively to the ULV.

In past practice, patients receiving an implantable cardioverter defibrillator (ICD) have undergone DFT testing in order to ensure a reasonable certainty of successful defibrillation using shock pulse energies corresponding to the output capacity of the ICD. The DFT has been determined by inducing fibrillation through delivery of a shock during the T-wave, then delivering defibrillation shocks to verify successful defibrillation at shock energies at least a safety margin below the maximum ICD output.

Determination of the ULV as a surrogate for DFT affords the opportunity to significantly reduce the number of times needed to induce fibrillation in a patient in order to ensure the patient's DFT falls below the maximum ICD output. The ULV, which can be measured in regular rhythm, corresponds to a shock strength that defibrillates with a high probability of success.

However, a challenge remains in determining the proper timing of a T-shock delivered to determine the ULV. If a T-shock is properly timed during the vulnerable period, and is greater than or equal to the ULV, fibrillation will not be induced. However, if a T-shock that is below the ULV is delivered just outside the vulnerable period, failure to induce fibrillation may lead to an incorrect determination of the ULV. Correct timing of T-shocks during the vulnerable period can be determined using 12-lead ECG signals by manually measuring the time interval between a test pacing pulse and a selected point on the T-wave. The ICD is then programmed to deliver a shock at that time interval. However, such techniques using 12-lead ECG signals are time-consuming and require considerable skill. A need remains, therefore, for automated methods for determining the correct timing of T-shock delivery for reliable ULV determination and DFT estimation.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
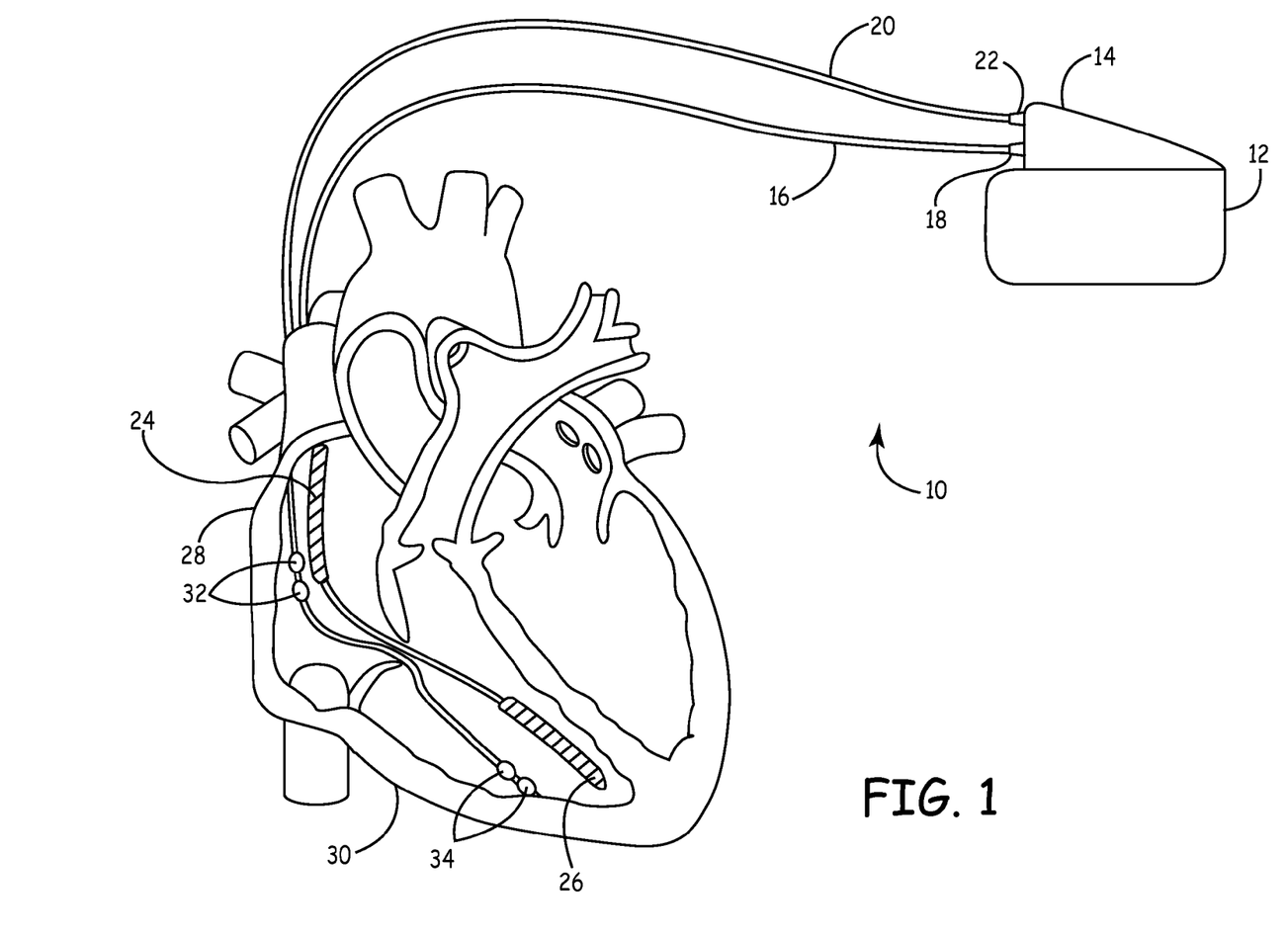
FIG. 1 is a plan view of an ICD coupled to a patient's heart via intracardial leads according to one embodiment of the present invention.

FIG. 1 is a plan view of an ICD coupled to a patient's heart via intracardial leads according to one embodiment of the present invention. ICD 10 includes a housing 12 for enclosing circuitry within ICD 10 and a connector block 14 for receiving an electrical connector 18 of high-voltage lead 16 and electrical connector 22 of pacing/sensing lead 20. High-voltage lead 16 carries a proximal coil electrode 24 and a distal coil electrode 26. High-voltage lead 16 is shown configured to position proximal electrode 24 along the right atrium 28 and/or along the superior vena cava (SVC) and position distal electrode 26 within right ventricle (RV) 30. Proximal electrode 24 is referred to hereafter as an "SVC coil electrode", and distal electrode 26 is referred to hereafter as "RV coil electrode". Alternatively, these two electrodes may be on different leads. SVC coil electrode 24, RV coil electrode 26 and the housing 12 of ICD 10 may be used in any combination for delivering a high-voltage shock pulse. A shock pulse may be delivered for determining the ULV or DFT at ICD implantation or follow-up or for delivering a defibrillation shock in response to detecting fibrillation.

Pacing/sensing lead 20, carries two sets of pacing/sensing electrodes, a proximal electrode set 32 positioned within the right atrium 28 and a distal electrode set 34 positioned within the right ventricle 30. Alternatively, electrode sets 32 and 34 may be on different leads or on the lead that carries either or both coil electrodes 24 and 26. As another alternative, separate electrode pairs may be used for right-ventricular pacing and sensing. In various embodiments of the invention, the leads, electrodes for delivering high-voltage shock pulses and electrodes for pacing and sensing may be intracardiac, epicardial, intravascular, subcutaneous or submuscular designs.

Because DFTs vary with electrode placement and lead configuration, as well as with the responsiveness of a particular patient's heart, the ULV is determined after the electrodes and leads have been placed at their intended implant positions. In this manner, the ULV corresponds to the patient and particular arrangement of the electrodes used.

Figure 2:
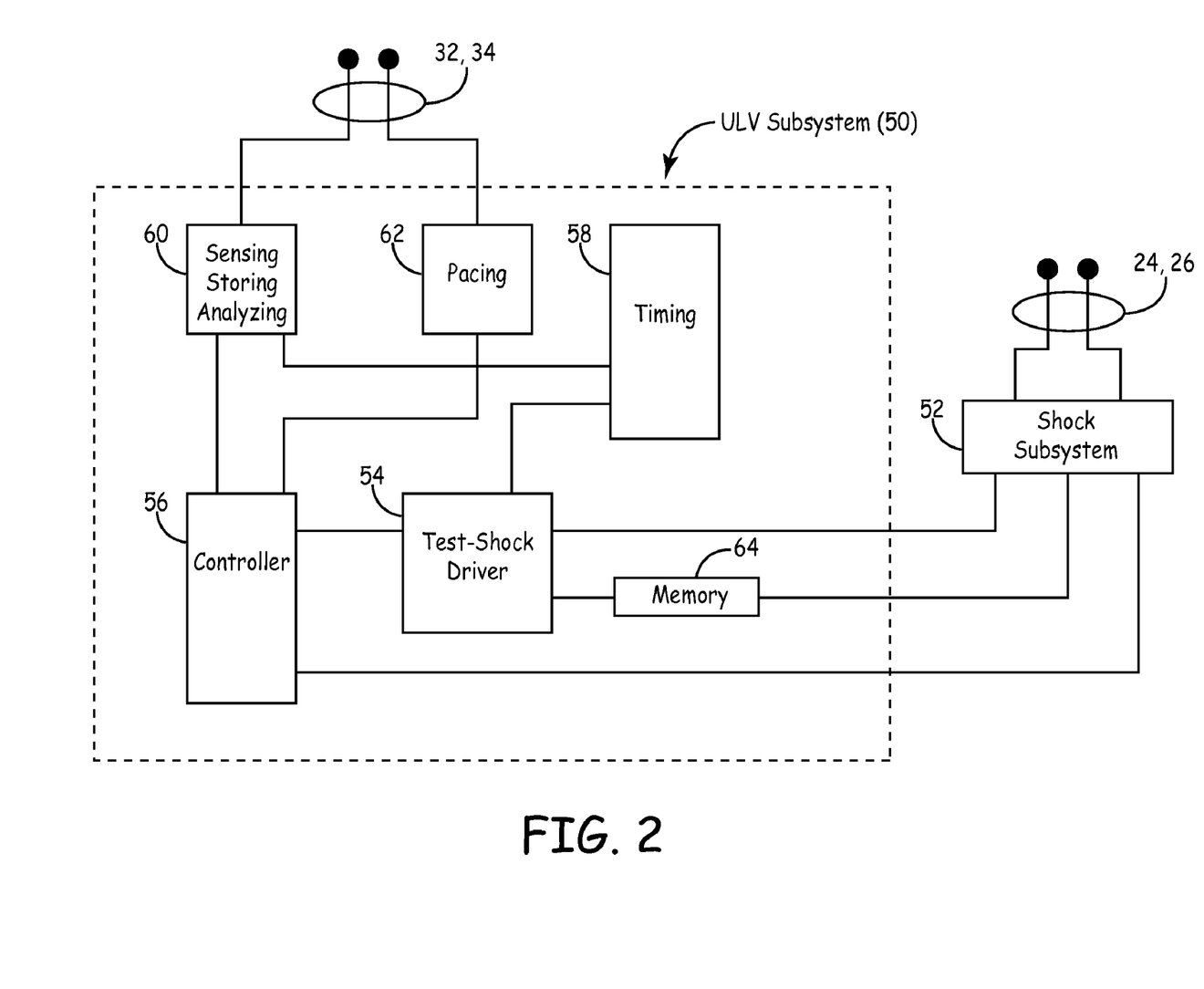
FIG. 2 is a functional block diagram of one embodiment of a ULV subsystem 50 in electrical connection with a shock subsystem 52.

FIG. 2 is a functional block diagram of one embodiment of a ULV subsystem 50 in electrical connection with a shock subsystem 52. ULV subsystem 50 and shock subsystem 52 are component subsystems of ICD 10 of FIG. 1 and are enclosed within housing 12 and electrically connected with other ICD circuitry and with ICD leads or electrodes as appropriate to achieve the desired functionality as described herein. ULV subsystem 50 includes a test-shock driver 54 for triggering T-wave shocks to be generated by shock subsystem 52. A control module 56 in combination with memory unit 64 and timing circuit 58 control test shock driver 54 and pacing circuit 62. A sensing, storing, and analyzing circuit 60 is provided for sensing, storing, and analyzing cardiac electrogram (EGM) signals.

Shock subsystem 52 is programmable to deliver monophasic or biphasic shocks, having variable tilt, and controllable through a stepwise range of energy outputs from, for example, at least 5 J to at least 30 J. When shock subsystem 52 is included in a subcutaneous ICD system relying on subcutaneous electrodes for defibrillating the heart, the output range may be substantially higher. Shock subsystem 52 is connected to the test shock driver 54, memory 64 and control module 56 of the ULV subsystem 50. Shock subsystem 52 is used to generate test shock pulses used in determining the ULV for a patient as well as generate defibrillation shocks in response to ICD detection of tachycardia or fibrillation.

ULV measurement techniques described herein are generally performed during cardiac pacing delivered by pacing circuit 62 under the control of timing circuit 58 at a rate slightly higher than an intrinsic heart rate determined by sensing, storing and analyzing circuit 60. Alternatively, pacing pulses may be delivered at a predetermined high rate, for example 120 bpm, expected to be above the patient's resting heart rate. The pacing circuit 62, however, is not necessary for embodiments of the invention which are operative during an intrinsic rhythm.

Control module 56 is set to control the delivery of pacing and shock delivery, providing an initial test-shock energy, and triggering sensing circuit 60 to detect the heart's intrinsic rate and transmit this rate value back to control module 56. The starting shock strength is stored in memory unit 64. The intrinsic heart rate value is passed to pacing circuit 62. Pacing circuit 62 then provides a baseline pacing output to electrode sets 32, 34 that is of a rate sufficient to overdrive the heart's intrinsic rate. The sensing, storing, and analyzing circuit 60 then evaluates an EGM signal, which represents the electrical activity of the heart.

The timing of pacing pulses may be transmitted to the sensing circuit 60 electronically. Alternatively, the sensing, storing, and analyzing circuit 60 may identify the pacing pulse during its evaluation of the EGM. Sensing, storing and analyzing circuit 60 may be further configured to evaluate EGM signals to detect capture following delivering of a pacing pulse by pacing circuit 62. Successful capture by pacing pulses may be verified by detecting an evoked response following the pacing pulse. EGM signals received by sensing, storing and analyzing circuit 60 may include signals sensed using a number of different configurations of implanted electrodes including, but not limited to, intracardiac, transvenous, epicardial, intravascular, subcutaneous, and submuscular leads. Examples of sensing lead combinations may include leads positioned to record signals from the superior vena cava, the right atrium, the right ventricle, the left ventricle and combinations of electrodes such as between a lead tip electrode and a defibrillation electrode or combinations including pairing leads from the right atrium or the superior vena cava to the right or left ventricles.

A series of ventricular pacing pulses, such as 8-15 pulses, are delivered at an overdrive pacing rate. As will be described in greater detail herein, the sensing, storing and analyzing circuit 60 senses the EGM signals following at least some of the pacing pulses and evaluates the T-waves to determine a T-wave center. The time interval between the pacing pulse and the T-wave center will be used in setting a test shock time interval for controlling the delivery of a T-wave shock for determining or estimating the patient's ULV.

Figure 3A:
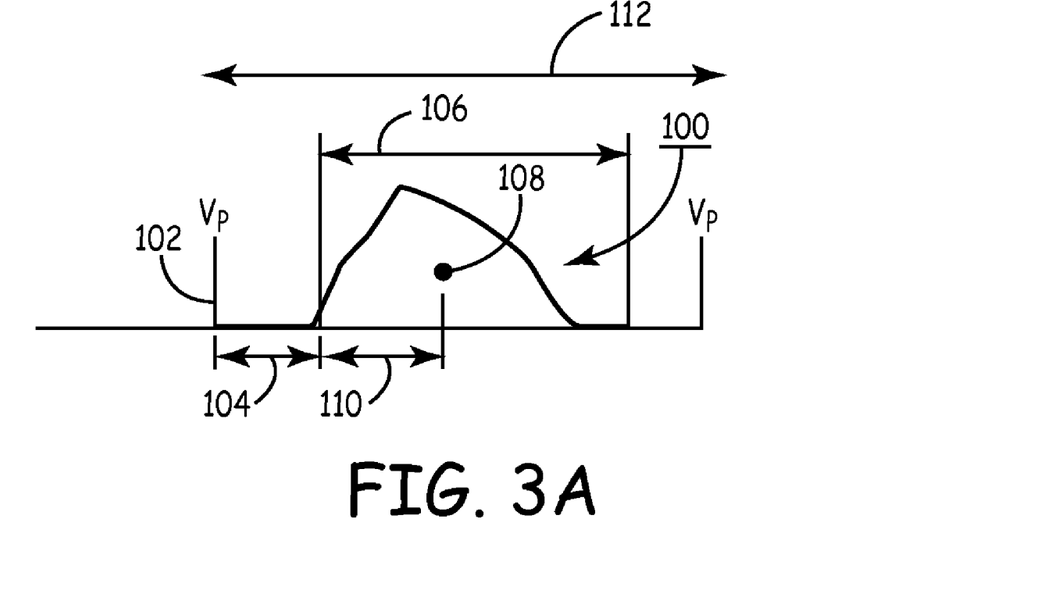
FIG. 3A is a diagram of a T-wave signal 100 sensed following a pacing pulse 102 illustrating one method for computing a T-wave shock time interval. A blanking period 104 is applied following the pacing pulse 102.

FIG. 3A is a diagram of a differentially filtered T-wave signal 100 sensed following a pacing pulse 102 illustrating one method for computing a T-wave shock time interval. A blanking period 104 is applied following the pacing pulse 102. A T-wave sensing window 106 is initiated at the end of the blanking period 104. The T-wave signal 100 sensed during the sensing window 106 is analyzed to determine the time interval 110 between the start of the T-wave sensing window to a T-wave center 108, referred to hereafter as the "T-wave center time point" ($T_{CP}$). In one embodiment, the T-wave center time point 108 is computed as the time point corresponding to a center of area of the T-wave. The center of the T-wave may be computed from sample points of the digitized T-wave or a time derivative of the T-wave. In one embodiment, the T-wave center time point may be computed by obtaining a differentially filtered T-wave signal then calculating a weighted point-by-point summation of the T-wave signal derivative sample points divided by the point-by-point summation of the T-wave signal derivative sample points as given by the following equation:

$$T_{CP} = \{\Sigma_{i=1, N}(i^*z(i))\} / \{\Sigma_{i=1, N}(z(i))\}$$

wherein $z(i)$ represents the amplitude of the $i^{th}$ sample point of the differentially filtered T-wave signal sample point and N is the number of signal sample points obtained during the T-wave sensing window 106.

Depending on the length of the T-wave sensing window 106 and the sampling rate, the number of signal sample points N may vary. In one example, the ventricular pacing pulse 102 is delivered at a pacing interval 112 set at 500 ms, the blanking period is set as 280 ms, and the T-wave sensing window 106 is 160 ms, with 40 points sampled during the sensing window 106.

A T-wave shock interval may be computed using the measured T-wave center time point 110. For example in one embodiment, a T-wave shock interval may be computed as the sum of the blanking interval 104 and the interval 110 from the start of the T-wave sensing window 106 to the T-wave center time point 110. It is recognized that the T-wave center time point 110 may be computed for multiple T-wave signals and the T-wave shock interval may be computed based on the average, median, maximum, minimum or other function of multiple T-wave center time point measurements. Furthermore, a T-shock interval may be computed based on the T-wave center time point and a predetermined offset or a percentage of the computed T-wave center time point interval.

Figure 3B:
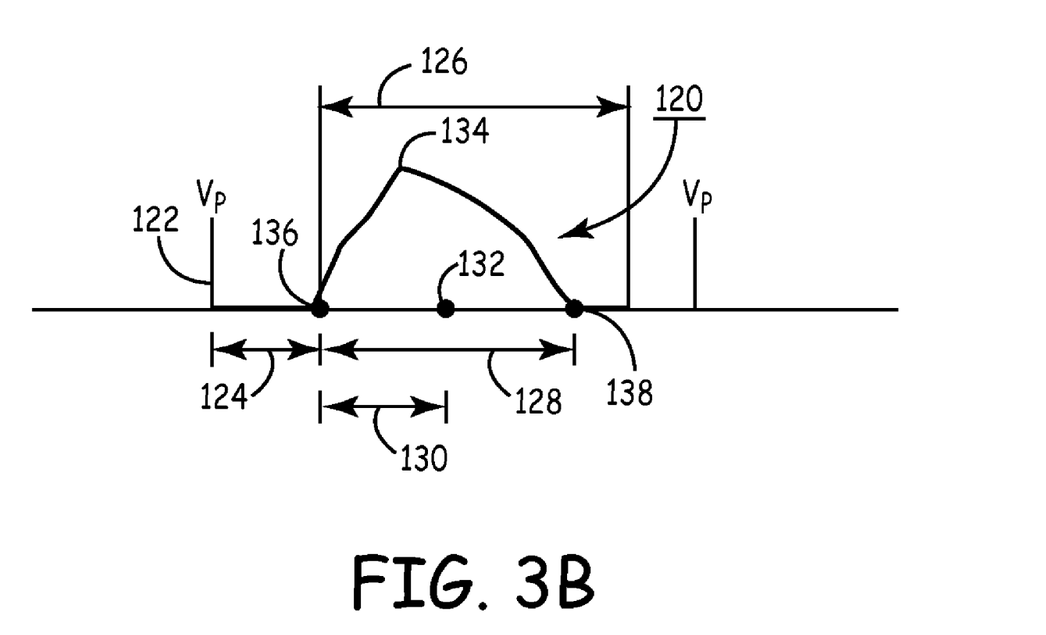
FIG. 3B is a diagram of a T-wave signal 120 sensed following a pacing pulse 122 illustrating another method for computing a T-wave shock time interval.

FIG. 3B is a diagram of a differentially filtered T-wave signal 120 sensed following a pacing pulse 122 illustrating another method for computing a T-wave shock time interval. In this example, the T-wave center is determined as the center 132 of the differentially filtered T-wave signal width 128. Accordingly, the T-wave signal 120 is sampled during T-wave sensing window 126, following a blanking period 124 applied upon delivery of ventricular pacing pulse 122. The T-wave width 128 is determined by searching before and after the T-wave signal peak 134 for zero-crossings of the T-wave signal. The signal peak 134 may be identified using peak detection methods and may be a positive or negative going peak.

Once a zero-point 136 is found preceding the signal peak 134 and a zero-point 138 is found succeeding the signal peak 134, a T-wave signal width 128 is computed. The center 132 of the T-wave width is determined as half the signal width 128. The T-wave center time interval 130 is then computed as the interval from the start of the T-wave sensing window 126 to the T-wave width center 132. A T-wave shock interval may then be computed using the $T_{CP}$ interval 130, e.g. as the sum of the blanking period 124 and $T_{CP}$ interval 130.

Figure 4:
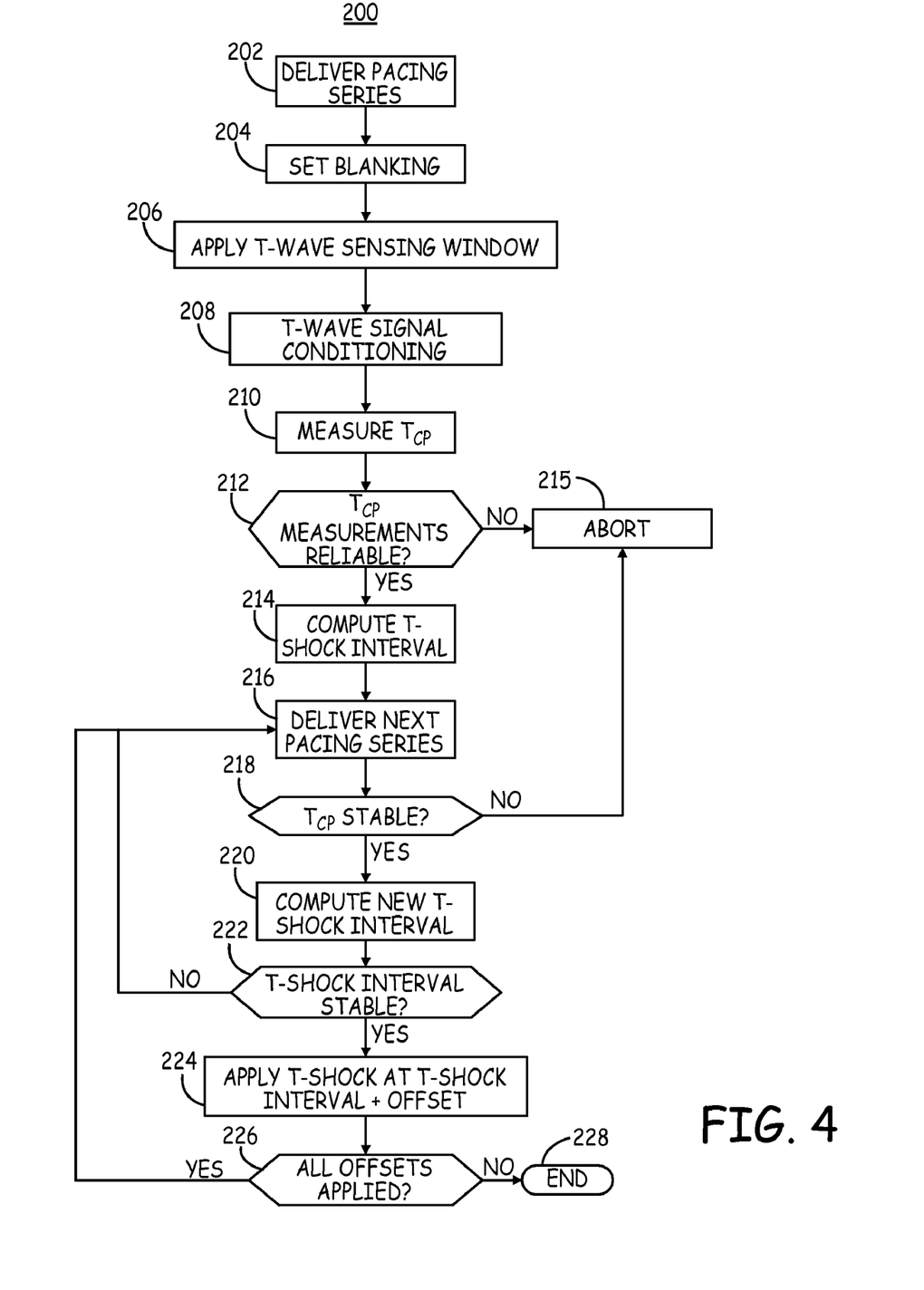
FIG. 4 is a flow chart of a method for delivering a T-wave shock for use in estimating a patient's defibrillation threshold.

FIG. 4 is a flow chart of a method for delivering a T-wave shock for use in estimating a patient's defibrillation threshold. A T-wave shock interval computed using the methods described herein is useful in any application requiring shock pulse delivery during the vulnerable period, which includes ULV and DFT measurement or estimation. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

Methods described in conjunction with flow charts and diagrams presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202 a series of ventricular pacing pulses is delivered at a pacing interval selected to overdrive pace the heart. Generally, a series of pacing pulses are applied to allow measurement of the ULV during a stable cardiac rhythm. A series of pacing pulses may include, for example 6 or more pacing pulses and typically include 8 pacing pulses. A blanking period is applied immediately following each pacing pulse at block 204.

A T-wave sensing window is applied at block 206 for sensing the T-wave following each blanking period. T-wave signal sensing may be performed using any available sensing electrode configuration. With reference to FIG. 1, T-wave signal sensing may be performed using the RV coil electrode 26 to the combination of the SVC coil electrode 24 and housing 12.

At block 208 the sensed T-wave signal is filtered and may undergo additional signal conditioning processes. Filtering may include band pass, low pass and differential filtering. In one embodiment, the EGM signal is band pass filtered at 3 to 100 Hz. The T-wave signal is further low pass filtered using a 12 Hz Butterworth filter. Signal filtering may include determining a T-wave signal time derivative and using the time derivative for computing a T-wave center. In one embodiment, differential filtering is performed using a five-point differential filtering method. In various embodiments, different filtering methods may be used for reducing high frequency noise.

Additional signal condition may include detecting the peak of the filtered T-wave signal and using the peak polarity for correcting signal sample points having the opposite polarity of the peak. In methods described herein for detecting a T-wave center of area or center of width, the peak amplitude polarity (i.e., positive or negative) of the differentially filtered T-wave signal may be used to set all other signal sample points having opposite polarity to zero values. In other words, if the maximum amplitude of the T-wave signal is a positive value, indicating a positive-going T-wave, all negative T-wave signal sample points are reset to zero. If the maximum T-wave amplitude is a negative value, indicating a negative-going T-wave, all positive T-wave signal sample points are set to zero. In this way, noisy sample points having opposite polarity from the T-wave polarity are removed.

At block 210, the center of the T-wave with respect to the start time of the T-wave sensing window, i.e. the $T_{CP}$ interval, is determined for one or more of the T-wave signals following the pacing pulses. The T-wave center time point interval may be determined using either of the algorithms described above, i.e., based on the center of the T-wave area or the center of the T-wave width. A T-wave center time point interval may be computed using a filtered T-wave signal, using a differential filtered T-wave, or using T-wave signal sample points that have undergone other signal conditioning methods.

At block 212, a reliability check may be performed to verify that the T-wave center time points measured for individual T-wave signals are consistent. A reliability check may include comparing two or more of the individually measured T-wave center time points. In one embodiment, the difference between two T-wave center time points may be compared to a reliability threshold. For example, during a series of eight ventricular pacing pulses, the difference between the T-wave center time points measured for the seventh and eighth pacing cycles may be compared to a reliability threshold of 40 ms. If the difference is greater than the reliability threshold, the T-wave center time point is deemed unreliable and may be discarded at block 215. The method 200 may be temporarily aborted and repeated at a later time by returning to block 202. It is recognized that numerous methods may be implemented to verify the reliability of T-wave center time point measurements. Such methods may include determining a standard deviation of $T_{CP}$ measurements or performing cross-checks between individual measurements or between individual measurements and an average of all individual measurements. The reliability threshold will be defined according to the reliability test methods used. Furthermore, it is recognized that different T-wave features, other than $T_{CP}$, may be determined for comparisons of T-wave signals for verifying reliability of the sensed signals.

The reliability check performed at block 212 may include performing capture verification for ensuring that T-wave measurements are made following pacing pulses that consistently capture the heart. A loss of capture during a pacing pulse series can produce anomalous T-wave center point measurements and result in an inappropriate T-wave shock interval. Capture verification may be performed by monitoring for an evoked response (QRS complex) during the blanking period following a pacing pulse. Capture verification methods are generally disclosed, for example, in U.S. Pat. No. 6,477,422 (Splett), hereby incorporated herein by reference in its entirety.

If the T-wave center time point measurements are determined to be reliable at block 212, a T-wave shock interval is computed at block 214 using the measured T-wave center time points. The T-wave shock interval may be computed using a percentage, average or median value of one or more T-wave center time point measurements. In one embodiment, the T-wave shock interval is computed as the blanking period applied following the pacing pulse plus an average of the T-wave center time point interval for the seventh and eight differential filtered T-wave signals measured during a series of eight pacing pulses.

At block 216, another series of pacing pulses is delivered. A stability verification may be performed at block 218 to verify that the cardiac rhythm as remained stable in terms of the T-wave center point since the T-wave shock interval was computed. For example, $T_{CP}$ measurements may be repeated on a subset (or all) of the EGM signals sensed following the pacing pulses using the same methods as used at block 210. The $T_{CP}$ measurements may be compared to the $T_{CP}$ measurements used for computing the T-shock interval, compared to the computed T-shock interval itself, or used to compute a new T-shock interval that is compared to the T-shock interval computed at block 214. If any of these comparisons result in a stability threshold being exceeded, the method 200 may be aborted at block 215, and repeated either immediately or at a later time by returning to block 202.

Alternatively if a new T-shock interval computed at block 220 is different than the previously computed T-shock interval, for example more than 20 ms greater than or less than the previously computed T-shock interval, method 200 may store the newly computed T-shock interval and return to block 216 to deliver another series of pacing pulses, without delivering a T-shock. The new T-shock interval is stored as the current T-shock interval and another new T-shock interval is computed at block 220 (after verifying stable $T_{CP}$ measurements at block 218. If the new T-shock interval is found to be approximately equal or within a predetermined threshold of the currently stored T-shock interval (as determined at block 222), a T-wave shock is delivered at block 224 at the stored T-shock interval plus a predetermined offset following the last pacing pulse of the current pacing pulse series.

It is recognized that multiple T-wave shocks may be delivered using multiple offsets following separate pacing pulse sequences so as to "scan" the T-wave with shock pulses and thereby reduce the likelihood of underestimating the ULV due to an improperly timed T-shock, i.e., outside the vulnerable period. An initial offset may be 0 ms such that the T-wave shock is delivered at the computed T-shock interval. Subsequent offsets may be negative and/or positive. In one embodiment, offsets include −20 ms, 0 ms, +20 ms and +40 ms. When multiple offsets are used, blocks 216 through 222 are repeated until all of the desired offsets have been applied in delivering a T-wave shock as determined at block 222. Method 200 then ends at block 224.

It is recognized that T-shocks may alternatively be delivered on the last pacing pulse of the initial pacing pulse series after computing the T-shock interval at block 214. Furthermore it is recognized that the T-wave center point measurements could be performed during an intrinsic cardiac rhythm. The T-wave shock interval is computed relative to a sensed R-wave and T-wave shocks are delivered following a sensed R-wave at the computed T-wave shock (plus any desired offset).

The results of the T-shock tests may then be used in estimating the patient's defibrillation threshold. In one embodiment, the T-shocks are delivered at a shock pulse energy that is a safety margin below the maximum ICD output. If fibrillation is not induced, the T-shock energy is considered to be above the patient's ULV, indicating a high probability of successful defibrillation at the tested T-shock energy. However, it is recognized that additional testing may be performed by delivering T-shocks at the computed T-shock interval and predetermined offsets at varying shock energies. For example, the T-wave shock may be delivered at each offset from the computed T-shock interval using a shock energy set to a high level thought to be well above the patient's ULV. The T-shocks may then be repeated at successively lower energy levels until fibrillation is induced. The lowest energy that fails to induce fibrillation is determined as the patient's ULV and can be used in determining if the patient meets ICD implant requirements and in programming a defibrillation shock energy.

Figure 5:
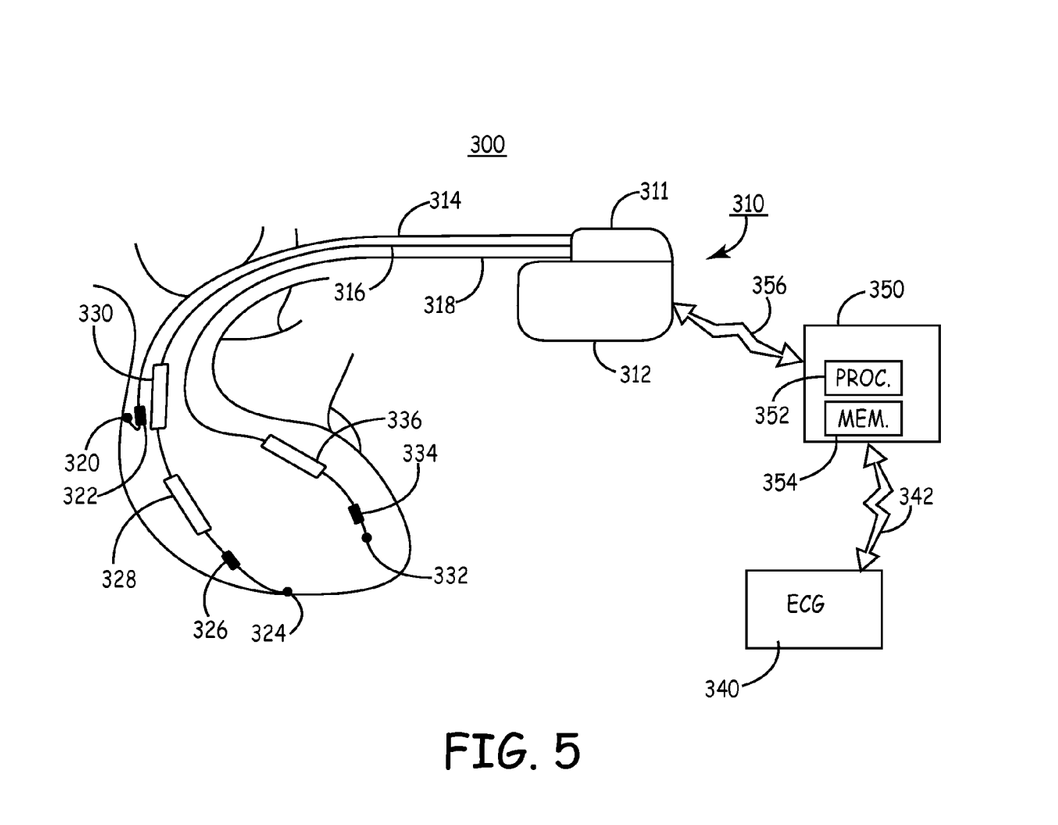
FIG. 5 is a schematic diagram of an alternative ICD system 300 in which the present invention may be embodied.

FIG. 5 is a schematic diagram of an alternative ICD system 300 in which the present invention may be embodied. ICD 310, having housing 312 which can be used as a CAN electrode, is coupled via connector block 311 to a right atrial (RA) lead 314, a right ventricular (RV) lead 316, and a left ventricular (LV) lead 318. RA lead includes a RA tip electrode 320 and a RA ring electrode 322 for pacing and sensing in the right atrium. RV lead 316 includes a RV tip electrode 324 and a RV ring electrode 326 for pacing and sensing in the right ventricle. RV lead 316 further includes a RV coil electrode 328 and an SVC coil electrode 330. LV lead 318 includes an LV tip electrode 332, an LV ring electrode 334, and an LV coil electrode 336. According to various embodiments of the present invention, any of electrodes 320 through 336 and housing 312 may be selected for use in sensing T-wave signals for determining a T-wave shock interval. A T-wave shock interval may be computed based on a time interval measured with respect to one or more features of sensed T-waves, such as a T-wave center as described above. Multiple sensing electrode configurations may be monitored sequentially or simultaneously for obtaining T-wave signal data for measuring such time intervals.

Furthermore, the pacing pulses delivered for determining a T-shock interval and prior to delivering a T-shock may be delivered using any available pacing electrodes. For example, a series of pacing pulses may be delivered using RV tip and ring electrodes 326 and 328 or using LV tip and ring electrodes 332 and 334.

In some embodiments of the invention, T-wave signals obtained using an external ECG leads, for example 12-lead ECG monitor 340, may also be analyzed for use in computing a T-shock interval. ECG signals from a 12-lead ECG monitor 340 may be provided via a hardwired or wireless communication link 342 to an external programmer 350. Programmer 350 includes a processor 352 and memory 354 for storing and processing 12-lead ECG signals. In one embodiment, programmer 350 measures intervals between pacing pulses and T-wave signal peaks. A baseline T-wave shock interval is derived from the 12-lead ECG signals based on the occurrence of T-wave signal peaks relative to delivered pacing pulses (or QRS signals). This baseline T-wave shock interval may be communicated to ICD 310 via wireless communication link 356 and used by ICD 310 for verifying or adjusting a T-wave shock interval automatically computed by ICD 310. Alternatively, the baseline T-wave shock interval may be used in selecting a sensing configuration for timing T-wave shocks delivered by ICD 310 based on the sensing configuration that results in a T-wave shock interval that most closely matches the baseline interval.

Figure 6:
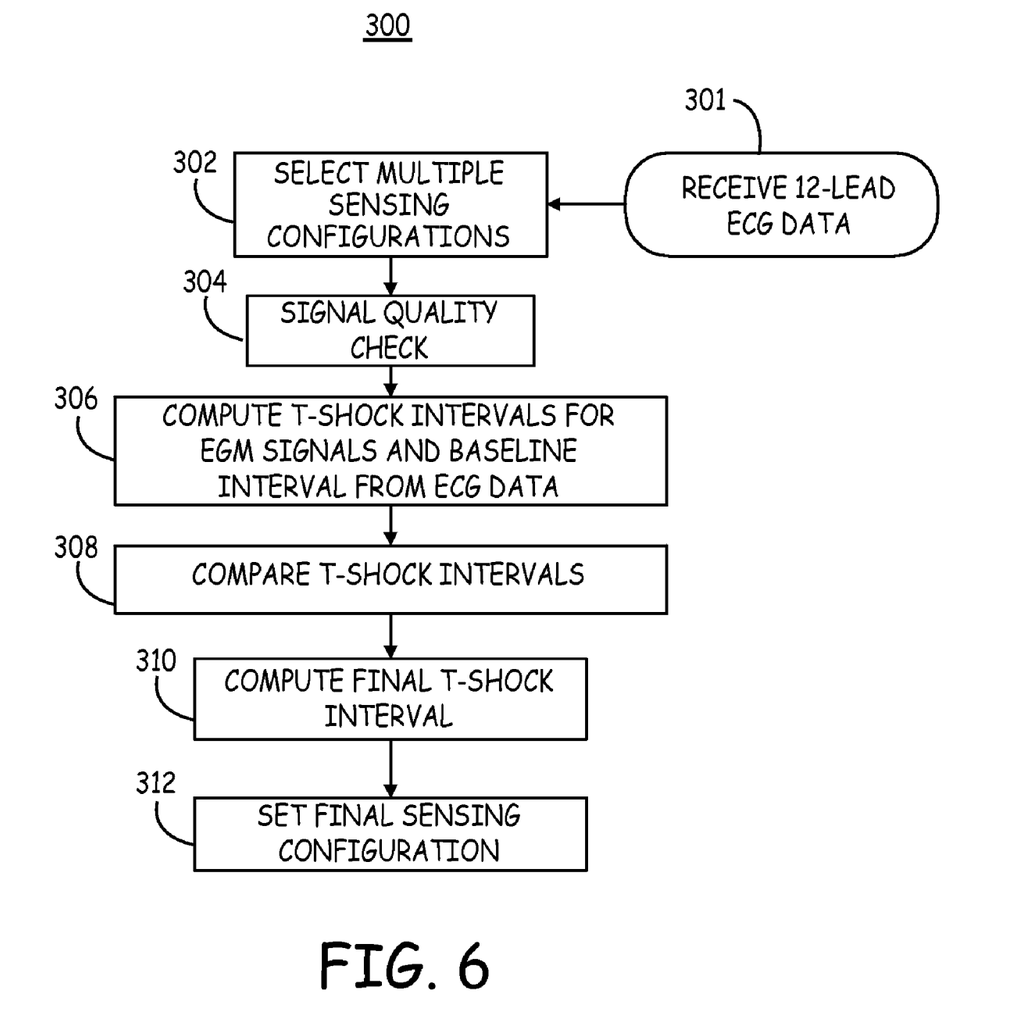
FIG. 6 is a flow chart of a method 300 for determining a T-wave shock interval using multiple sensing configurations.

FIG. 6 is a flow chart of a method 300 for determining a T-wave shock interval using multiple sensing configurations. At block 302, multiple sensing configurations are selected using available implanted electrodes. External ECG data may additionally be received as indicated by block 301. ECG data may be received by the ICD via a programmer as shown in FIG. 5. The programmer may process the 12-lead ECG data and compute a baseline T-wave shock interval based on the 12-lead ECG signals. The baseline T-wave shock interval is then be transmitted to the ICD. Alternatively, digitized 12-lead ECG data may be transmitted directly to the ICD via a programmer or other wireless communication link and analyzed by the ULV subsystem controller of the ICD for determining a baseline T-wave shock interval.

At block 304, a signal quality check may be performed to verify reliable signal quality for the selected sensing configurations. Any signal having an unacceptable frequency content, unacceptable T-wave variability, or unacceptable T-wave center time point measurement differences as compared to other sensing configurations may be rejected for use in determining a final T-wave shock interval.

In one embodiment, the reliability of T-wave center time point measurements for each sensing configuration may be determined. For example, comparisons between T-wave center time point measurements may be made on a beat-by-beat basis for determining the stability of an individual sensed signal. Alternatively, comparisons between single beat measurements and an overall average T-wave center time point measurement may be made to determine if an individual sensing configuration is acceptably stable. For example, beat-by-beat T-wave center time point measurements may be required to be within 15 ms of each other in order to accept the sensing configuration. Alternatively, the sensing electrode configuration resulting in the least variability of T-wave center time point measurements may be selected for use in determining a T-wave shock interval.

In yet another embodiment, the frequency content of T-wave signals for multiple sensing configurations is evaluated and one or more sensing configurations having the lowest high-frequency signal content are selected for use in determining a final T-shock interval. In still another embodiment, the signal quality check performed at block 304 may include capture verification methods for ensuring that T-wave measurements are made following pacing pulses that consistently capture the heart.

At block 306, T-shock intervals are computed for each of the sensing configurations having acceptable signal quality or a single sensing configuration determined to have the best signal quality. The T-wave shock interval(s) may be computed using the T-wave center time point methods described above. At block 308, the computed T-wave shock interval(s) for each selected sensing configuration are compared. The comparison made at block 308 may include a comparison to a baseline T-wave shock interval derived from the 12-lead ECG data. A final T-shock interval is computed at block 310 based on the comparison at block 308. A final sensing configuration for timing T-wave shock delivery is then set at block 312 based on the final T-shock interval.

In one embodiment, a final T-wave shock interval to be applied during T-wave shock delivery may be determined as a maximum, minimum, mean, or median T-wave shock interval computed for multiple sensing configurations. When a single sensing configuration is selected in response to the signal quality check at block 304, the final T-wave shock interval is the T-wave shock interval computed for the selected sensing configuration. Computation of the final T-wave shock interval may include an adjustment of a computed T-wave shock interval based on the baseline T-wave shock interval derived from external ECG data. For example, a T-wave shock interval computed using T-wave center time point measurements from implanted electrode signals may be adjusted to equal a baseline T-wave shock interval. Alternatively, the sensing configuration resulting in a T-wave shock interval that most closely matches the baseline T-wave shock interval may be selected as the final sensing configuration and the corresponding T-wave shock interval used as the final T-wave shock interval.

Thus, a method and apparatus for delivering T-wave shocks have been presented in the foregoing description with reference to specific embodiments. It is appreciated that various modifications to the referenced embodiments may be made without departing from the scope of the invention as set forth in the following claims.

The invention claimed is:

1. A method, comprising:
   sensing a cardiac electrogram (EGM) signal comprising a T-wave signal;
   detecting a first zero crossing of the T-wave signal before a peak of the T-wave signal;
   detecting a second zero crossing of the T-wave signal after the peak of the T-wave signal;
   determining a width of the T-wave signal as an elapsed time between the first zero crossing and the second zero crossing;
   determining a center of the T-wave signal as a time corresponding to half of the determined width of the T-wave signal;
   determining a test shock interval based on the determined T-wave signal center; and
   scheduling a T-wave shock to be delivered at a T-wave shock interval corresponding to the determined test shock interval; and
   delivering the T-wave shock to a patient at the T-wave shock interval.

2. The method of claim 1 wherein determining the T-wave signal center comprises determining a time derivative of the T-wave signal.

3. The method of claim 1 wherein sensing the EGM signal comprises delivering a first series of pacing pulses and sensing the T-wave signal during a sensing window following each of the pacing pulses and further comprising:
   determining a feature of the T-wave signal sensed following at least two pacing pulses in the first series of pacing pulses,
   determining a difference between the at least two T-wave signal features; and
   determining the test shock interval in response to the difference being less than a predetermined threshold.

4. The method of claim 3 further comprising:
   delivering a second series of pacing pulses;
   determining a feature of the T-wave signal sensed during the second series of pacing pulses;
   comparing the T-wave signal feature determined during the second series of pacing pulses to the T-wave signal features determined during the first series of pacing pulses; and
   selecting one of delivering the T-wave shock and canceling the T-wave shock in response to the comparison between the T-wave signal feature determined during the second series of pacing pulses and the T-wave signal features determined during the first series of pacing pulses.

5. The method of claim 4 further comprising:
   determining a center of a T-wave signal during the second series of pacing pulses;
   determining a new test shock interval based on the T-wave signal center determined during the second series of pacing pulses;
   comparing the new test shock interval determined during the second series of pacing pulses to the test shock interval determined during the first series of pacing pulses; and
   storing the new test shock interval in response to canceling the T-wave shock.

6. The method of claim 1 further comprising:
receiving external electrocardiogram (ECG) data;
automatically determining a baseline T-wave shock interval from the ECG data;
comparing the test shock interval determined from the EGM signal and the baseline T-wave shock interval determined from the ECG signal; and
determining a final T-wave shock interval in response to the comparing.

7. The method of claim 6 wherein sensing a cardiac EGM signal comprises:
selecting a plurality of EGM sensing configurations;
determining a signal quality for each of the plurality of sensing configurations; and
selecting a cardiac EGM sensing configuration based on the signal quality;
wherein determining the signal quality comprises determining a test shock interval for each of the plurality of sensing configurations and selecting the cardiac EGM sensing configuration comprises comparing the determined test shock intervals for each of the plurality of sensing configurations to the baseline T-wave shock interval and selecting an EGM sensing configuration corresponding to a test shock interval closest to the baseline T-wave shock interval.

8. The method of claim 7 further comprising delivering a series of pacing pulses wherein the EGM signal is sensed following the pacing pulses and wherein determining the signal quality comprises verifying capture of the pacing pulses.

9. A medical device system, comprising:
electrodes for sensing a cardiac electrogram (EGM) signal comprising a T-wave signal;
a sensing circuit coupled to the electrodes for receiving the EGM signal;
a control module coupled to the sensing circuit and configured to:
detect a first zero crossing of the T-wave signal before a peak of the T-wave signal,
detect a second zero crossing of the T-wave signal after the peak of the T-wave signal,
determine a width of the T-wave signal as an elapsed time between the first zero crossing and the second zero crossing,
determine a center of the T-wave signal as a time corresponding to half of the determined width of the T-wave signal, and determine a test shock interval based on the determined T-wave signal center;
a memory for storing the test shock interval; and
a shock generating circuit coupled to the control module for delivering a T-wave shock to a patient's heart at a T-wave shock interval corresponding to the stored test shock interval.

10. The system of claim 9 wherein determining the T-wave signal center comprises determining a time derivative of the T-wave signal.

11. The system of claim 9 further comprising a pacing circuit coupled to the control module and the sensing circuit,
wherein the control module is configured to control the pacing circuit to deliver a first series of pacing pulses and control the sensing circuit to sense the EGM signal during a sensing window corresponding to the T-wave signal following each of the pacing pulses and further configured to:
determine a feature of the T-wave signal sensed following at least two pacing pulses in the first series of pacing pulses,
determine a difference between the at least two T-wave signal; features and
determine the test shock interval in response to the difference being less than a predetermined threshold.

12. The system of claim 11 wherein the control module is further configured to control the pacing circuit to deliver a second series of pacing pulses,
wherein the T-wave shock is delivered at the T-wave shock interval corresponding to the test shock interval following a last pacing pulse of the second series of pacing pulses,
wherein the sensing circuit is configured to sense a T-wave signal during the second series of pacing pulses, and
wherein the control module further configured to determine a feature of the T-wave signal sensed during the second series of pacing pulses and compare the T-wave signal feature determined during the second series of pacing pulses to the T-wave signal features determined during the first series of pacing pulses, and select one of delivering the T-wave shock and canceling the T-wave shock in response to the comparison between the T-wave signal feature determined during the second series of pacing pulses and the T-wave signal features determined during the first series of pacing pulses.

13. The system of claim 12 wherein the control module is further configured to determine a T-wave signal center during the second series, determine a new test shock interval in response to the T-wave signal center determined during the second series of pacing pulses, compare the new test shock interval determined during the second series of pacing pulses to the stored test shock interval determined during the first series of pacing pulses, and store the new test shock interval in response to canceling the T-wave shock.

14. The system of claim 9 further comprising:
a telemetry circuit for receiving external electrocardiogram (ECG) data, the telemetry circuit in communication with the control module; and
a processor configured to automatically determine a baseline T-wave shock interval from the ECG data;
wherein the control module is configured to compare the test shock interval determined from the EGM signal and the baseline T-wave shock interval determined from the ECG signal and determine the T-wave shock interval corresponding to the test shock interval in response to the comparing.

15. The system of claim 14 wherein the control module is further configured to:
control the sensing circuit to select a plurality of EGM sensing configurations;
determine a signal quality for each of the plurality of sensing configurations; and
select a cardiac EGM sensing configuration in response to the signal quality; quality,
wherein the control module determines the signal quality by at least determining a test shock interval for each of the plurality of EGM sensing configurations, and selects the cardiac EGM sensing configuration by at least comparing the test shock interval determined for each of the plurality of EGM sensing configurations to the baseline T-wave shock interval and selecting an EGM sensing configuration corresponding to a test shock interval closest to the baseline T-wave shock interval.

16. The system of claim 15 further comprising a pacing circuit for delivering pacing pulses, wherein the EGM signal is sensed following the pacing pulses and wherein determining the signal quality comprises verifying capture of the pacing pulses.

17. A non-transitory computer readable medium for storing a set of instructions which when implemented in a medical device system cause the system to:
- sense a cardiac electrogram (EGM) signal comprising a T-wave signal;
- detect a first zero crossing of the T-wave signal before a peak of the T-wave signal;
- detect a second zero crossing of the T-wave signal after the peak of the T-wave signal;
- determine a width of the T-wave signal as an elapsed time between the first zero crossing and the second zero crossing;
- determine a T-wave center of the T-wave signal as a time corresponding to half of the determined width of the T-wave signal;
- determine a test shock interval based on the determined T-wave signal center;
- schedule a T-wave shock to be delivered at a T-wave shock interval corresponding to the determined test shock interval; and
- deliver the T-wave shock to a patient at the T-wave shock interval.

* * * * *